United States Patent [19]

Cavazza

[11] Patent Number: 4,464,393

[45] Date of Patent: Aug. 7, 1984

[54] USE OF ALKANOYL L-CARNITINES IN THE THERAPEUTICAL TREATMENT OF MYOPATHIES AND MUSCULAR DYSTROPHIES

[75] Inventor: Claudio Cavazza, Rome, Italy

[73] Assignee: Sigma-Tau Industrie Farmaceutiche Riunite S.p.A., Rome, Italy

[21] Appl. No.: 558,107

[22] Filed: Dec. 5, 1983

[30] Foreign Application Priority Data

Dec. 9, 1982 [IT] Italy .............................. 49644 A/82

[51] Int. Cl.$^3$ ......................................... A61K 31/205
[52] U.S. Cl. .................................................. 424/316
[58] Field of Search ........................................ 424/316

[56] References Cited

U.S. PATENT DOCUMENTS 3,830,931  8/1974  De Felice ............................ 424/319
4,343,816  8/1982  Cavazza ............................. 424/316
4,346,107  8/1982  Cavazza et al. ..................... 424/316

*Primary Examiner*—Stanley J. Friedman
*Attorney, Agent, or Firm*—Bruce M. Collins

[57] ABSTRACT

A novel therapeutical use of some alkanoyl L-carnitines, e.g. acetyl L-carnitine, is disclosed which, orally or parenterally administered, are effective in the treatment of secondary and congenital muscular dystrophies and myopathies.

2 Claims, No Drawings

USE OF ALKANOYL L-CARNITINES IN THE THERAPEUTICAL TREATMENT OF MYOPATHIES AND MUSCULAR DYSTROPHIES

The present invention relates to a novel therapeutical utilization of some alkanoyl L-carnitines. More specifically, it relates to the use of alkanoyl L-carnitines having general formula

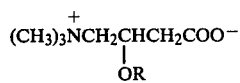

wherein R is selected from acetyl, propionyl, butyryl, hydroxy-butyryl, valyl and iso-leucyl, and their pharmacologically acceptable salts, for the therapeutical treatment of myopathies and muscular dystrophies, both congenital (e.g. Duchenne muscular dystrophy) and secondary (e.g. toxic dystrophy and disuse atrophy). The invention also relates to orally or parenterally administrable pharmaceutical compositions which contain the above-identified alkanoyl L-carnitines as active principles for the treatment of the previously mentioned pathologies. In the description which follows, reference will be made, for the sake of simplicity, to acetyl L-carnitine, it being, however, understood that the disclosures concerning this specific compound equally apply to the other mentioned alkanoyl derivatives of carnitine.

Previous therapeutical uses of acetyl L-carnitine and other alkanoyl derivatives of carnitine are already known. For instance, the U.S. Pat. No. 4,194,006 discloses the use of acetyl carnitine in the therapeutical treatment of myocardial arrhythmias and ischemias. The U.S. Pat. No. 4,343,816 discloses the use of acetyl carnitine in the therapeutical treatment of functional peripheral vascular diseases of arteries, such as Reynaud's disease and acrocyanosis. The U.S. Pat. No. 4,346,107 discloses the therapeutical effectiveness of acetyl carnitine in the treatment of patients suffering from impaired cerebral metabolism as it occurs in senile and pre-senile dementia.

Acetyl-carnitine

Acetyl-carnitine

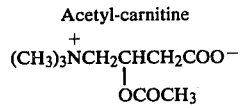

is structurally related to carnitine

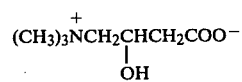

Carnitine deficiency in muscular tissues has long since been associated with an excessive lipid accumulation within the muscle fibre and identified as the etiological factor in several cases of myopathies.

In fact, as early as 1973, Engel and Angelini reported (Science, 173, 899-902, 1973) on a first case of myopathy brought about by muscle carnitine deficiency resulting in excessive triglyceride storage in the muscle paralleled by normal carnitine levels in plasma and liver; this syndrome was called "type 1 lipid storage myopathy" by the authors.

Subsequently, Karpati described (in Neurology, 25, 16-24, 1975) the first case ever known of myopathy provoked by systemic carnitine deficiency in an 11-year old boy. The patient showed excessive lipid storage in muscle cells and carnitine levels lower than normal in both plasma, liver and skeletal muscle.

In the decade elapsed since Engel and Angelini reported on the first ever recognized human example of carnitine deficiency, quite a number of myopathy and muscular dystrophy cases have been identified, which are ascribable either to carnitine deficiency in skeletal muscle (type 1 lipid storage myopathy) or to systemic carnitine deficiency.

The study of the clinical cases reported in the scientific literature reveals that in non-treated cases patient's death inevitably occurs, whereas in carnitine-treated patients strikingly beneficial effects are obtained in most cases.

In some cases, however, even carnitine or, particularly, L-carnitine administration has shown to be ineffective to resolve the pathological picture. In fact, there have already been several clinical cases reported wherein carnitine administration proved not to lead to any satisfactory therapeutical results from the very beginning of the treatment; in a number of other cases, after a feeble improvement in the initial period of the therapy, no further noticeable progress was then detected, whereas in some other instances, a steady regression to the initial conditions had to be recognized.

The already mentioned structural relationship between carnitine and acetyl-carnitine and the fact that acetyl-carnitine has frequently been shown to possess pharmacological activities which are comparable to those of L-carnitine at least from a qualitative standpoint, (see e.g. the activity toward the cardiac arrhythmias) would not have led to foresee markedly substantial differences in therapeutical effectiveness and activity of the two compounds in those cases of myopathies and muscular dystrophies which have shown to be non-respondent to L-carnitine treatment.

It has now been found surprisingly, that acetyl L-carnitine is strikingly effective in the treatment of myopathies and muscular dystrophies, both congenital and secondary, also in those cases which are L-carnitine non-respondent, i.e. when L-carnitine fails to achieve its intended therapeutical result.

On the grounds of this finding, the object of the present invention is a novel therapeutical use of acetyl L-carnitine, which comprises orally or parenterally administering to a human affected by myopathy or muscular dystrophy an amount of acetyl L-carnitine sufficient to induce in the human an anti-myopathic or anti-dystrophic effect.

Although the daily dose to be administered depends on the age, weight and general condition of the subject, utilizing sound professional judgment, it has been found that, generally, from about 10 to about 30 mg of acetyl L-carnitine/Kg of body weight/day or an equivalent amount of a pharmacologically acceptable salt thereof, is a suitable dose. However, larger doses can be safely administered in view of the low toxicity of the compound.

Acetyl L-carnitine is compounded into the pharmaceutical compositions by using the usual excipients, diluents and adjuvant agents which are well-known in pharmaceutical technology for preparing orally and parenterally administrable compositions. An extensive list of such excipients and adjuvant agents as well as the methods for preparing solid and liquid oral unit dosage forms such as tablets, capsules, solutions, syrups and the like and fluid injectable forms such as sterile solutions, is disclosed in the U.S. Pat. No. 3,830,931 to De Felice.

It has also been found that a pharmaceutical composition in unit dosage form which is particularly suited for the foregoing therapeutical uses comprises from about 500 to about 1,000 mg of acetyl L-carnitine.

Some non-limiting examples of pharmaceutical compositions suitable for oral and parenteral administration are illustrated hereinbelow:

| TABLETS | |
|---|---|
| Acetyl L-carnitine.HCl | mg 586 (corresponding to 500 mg of inner salt) |
| Polyvinylpyrrolidone | mg 60 |
| AVICEL PH 101 | mg 17 |
| Magnesium stearate | mg 20 |
| Cellulose acetophtalate | mg 18 |
| Ethyl phtalate | mg 7.5 |
| Silicone oil AK 100 | mg 3 |
| CAPSULES | |
| Acetyl L-carnitine | mg 586 (corresponding to 500 mg of inner salt) |
| AEROSIL 200 | mg 6 |
| Magnesium stearate | mg 25 |
| 5 gram-SACHETS | |
| Acetyl L-carnitine | mg 1,172 (corresponding to 1,000 mg of inner salt) |
| Sodium citrate | mg 300 |
| METHOCEL E 5 | mg 100 |
| Levulose | mg 1,500 |
| AEROSIL 200 | mg 25 |
| Saccarose, balance to | mg 5,000 |
| 5 ml - INJECTABLE PHIALS | |
| Lyophilized ingredients: | |
| Acetyl L-carnitine | mg 586 (corresponding to 500 mg of inner salt) |
| Glycocoll | mg 750 |
| Solvent: | |
| Water for injections | ml 5 |

It is not intended, nor is it necessary, to be bound to any theoretical interpretation of the biochemical mechanisms that are at the basis of the lower activity or the absence of any activity at all of L-carnitine with respect to the acetyl L-carnitine in the treatment of some cases of myopathies and muscular dystrophies. It can be postulated, however, that these activity discrepancies are related to some impairment in the enzyme system (specifically, a deficiency in Carnitine Acetyl Transferase) which controls the transfer of the acetyl groups from Coenzyme A to carnitine and the attendant acetyl utilization for energy production. Obviously, acetyl L-carnitine would not need Carnitine Acetyl Transferase to get to the utilization sites.

Some clinical cases illustrating the novel therapeutical use of acetyl L-carnitine according to the present invention are described herebelow.

It will be noted that in all the clinical cases illustrated the patient had been treated for a certain period of time with L-carnitine without attaining beneficial effects.

CLINICAL CASE 1

G. S., male, 42 years old—complex familial myodystrophy syndrome consistent in palpebral ptosis, eye movements impeded by akinesis of all the extrinsic ocular muscles. Moderate hypokinesis of the mimic musculature. Hyposthenia and hypotrophia of the muscle of the shoulder girdle worsening beginning at 30 years. At 41 the patient had to stop working due to the impossibility of raising his arms even for brief periods. In addition he complained of a profound generalized asthenia and signs of myocardial pain. The EKG showed a block in the right branch. He underwent therapy, without success, essentially cortisones and amino acid cocktails. Finally, after being studied in the proper neurological environment he underwent L-carnitine treatment. Such treatment lasted about a year, but the patient, contrary to expectations, found it to no avail. It was decided to suspend the treatment and to substitute it with acetyl L-carnitine.

The effect of the new therapy was surprising. Already after two weeks, he noted a remarkable improvement in the asthenia and gradually in the days which followed he began to regain muscular strength in his arms.

Two months after the beginning of therapy he was able to return to his job as a photocopy machine operator in a factory, and in the occasion of a visit to another city he carried 2 suitcases by himself during the trip. After 8 months the patient is in excellent mobile and muscular conditions. He is now working as switchboard operator, a job requiring a certain mobility in the arms.

The palpebral ptosis and akinesis of the eye muscles did not improve as they are due to a nervous transmission defect and not to primary myopathy. In compensation the electrocardiographic signs of myocardial pain disappeared.

CLINICAL CASE 2

M. F., male—64 years old. Since childhood he could hardly tolerate any physical fatigue. His legs were particularly weak and the thighs showed signs of hypotrophy. Nevertheless, the patient was able to lead a normal life until the age of 50, when general asthenia and the tendency to muscular exhaustion worsened more and more rapidly to the point where he was forced to discontinue his work as director of a farm. At 60 he was hardly able to walk or drive his car because, his arm muscles had also begun to weaken. Eventually, he turned to a neurologist and was diagnosed as having moderate hypotrophy and hyposthenia of the muscles of the shoulder girdle and marked hypotrophy and hyposthenia of the thigh and leg muscles brought about by primary myopathy since nervous conduction turned out to be normal.

In spite of his neurologist's advice, the patient turned down any therapy because he mistrusted medicines and from time to time he had to be taken to work in a wheelchair.

However, since he was so determined to run his farm as in the past, he eventually agreed to undergo L-carnitine therapy, 2 g a day.

After 2 months of treatment, a slight improvement in his general condition and a gain in weight was noticed, but his legs and arms did not improve.

At this time, the patient was administered acetyl L-carnitine, orally, 1.5 g a day. The beneficial effects of the drug were immediately evident, encouraging the patient to keep on with the therapy. After a few days the general asthenia decreased and his legs and arms recovered strength.

After four months of therapy he was fully self-sufficient and to some extent could bear fatigue.

After eight months he resumed driving his car to go to work. After a year and a half the effects of acetyl L-carnitine became constant and the patient is now able to lead an all but normal life. He still experiences a certain tendency to weariness, but he can work for a few hours both in the morning and in the afternoon. His muscular hypotrophy has markedly decreased.

CLINICAL CASE 3

M. M., female, 16 years old—normal psychomotor development up to 7 years of age. From that time a muscular weakness in the legs and arms began to develop which worsened gradually until, at the age at 10, the patient could no longer walk nor raise her arms.

Throughout this time she was treated with polyvitamins. Hospitalized in a neurological center, the patient was diagnosed as having congenital muscular dystrophy with lipid storage in the muscles. She underwent L-carnitine therapy, 3 g a day orally, and her condition improved gradually until in the 8th month of treatment she began to walk again by herself and to use her arms normally. A tendency toward becoming easily exhausted persisted which precluded every kind of strain and the patient was forced to rest for long periods during the day.

Nevertheless, considering the patient's grave condition at the onset of illness, the result was considered satisfactory and in that way she reached age 14 conducting an all but normal life.

Subsequently, the patient suffered temporary crises of muscular weakness which restricted arm and leg movements, forcing her into absolute rest.

Such crises would last for a day or two after which time the patient would recover fairly well and, gathering her forces, she was able to move and attend school, abstaining from any and every kind of strain such as gymnastics and long walks.

She went on this way for about a year until one of the above-mentioned crises lasted longer than usual and brought her back almost to the condition she was in at age 10 when she literally could not stay on her feet or raise her arms. L-carnitine treatment was then substituted by 2 g a day, orally, of acetyl L-carnitine.

The new therapy permitted the patient to rapidly get over the acute crisis. In fact, after 10 days, the patient was able to start walking again and to freely move her arms. She was still, as usual, easily tired. Treatment was continued reducing the dosage to 1.6 g a day. The patient visibly regained her strength and became aware that she could move better; she began to reduce her daily rest period and began to allow herself a little extra effort which until then was unthinkble for her. During vacation she would take long walks and could even hazard a swim.

On the reopening of school she was able to attend gym class. The neurological visit subsequently confirmed an objective improvement in the trophism of the muscular masses owing in part to the therapy and in part to the exercise that the therapy permitted.

After 2 years from the beginning of the new therapy the patient continues to lead a completely normal life and no longer needs to rest during the day, her nightly sleep being sufficient to recover her strength.

What is claimed is:

1. A method of treating a human affected by myopathy or muscular dystrophy which comprises orally or parenterally administering to the human in a single or multiple dose administration regimen an amount of an alkanoyl L-carnitine of formula

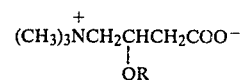

wherein R is selected from the group consisting of acetyl, propionyl, butyryl, hydroxy-butyryl, valyl and isoleucyl, or a pharmaceutically acceptable salt thereof, which is sufficient upon administration according to said regimen to achieve in said patient an anti-myopathic or anti-dystrophic effect.

2. The method of claim 1, wherein the total amount administered per day per Kg of body weight is from about 10 to about 30 mg of at least one member selected from the group consisting of the alkanoyl L-carnitines of formula

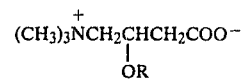

wherein R is selected from the group consisting of acetyl, propionyl, butyryl, hydroxy-butyryl, valyl and isoleucyl, or an equivalent amount of a pharmaceutically acceptable salt thereof.

* * * * *